(12) United States Patent
Ullrich et al.

(10) Patent No.: US 10,551,176 B2
(45) Date of Patent: Feb. 4, 2020

(54) SENSOR DEVICE AND METHOD OF INSPECTING THE SURFACE OF A CYLINDRICAL HOLLOW ENCLOSURE

(71) Applicant: Sturm Maschinen- & Anlagenbau GmbH, Salching (DE)

(72) Inventors: Wolfgang Ullrich, Starnberg (DE); Wolfgang Janetzki, Feldafing (DE); Philip Klinger, München (DE); Florian Bader, Pießenberg (DE)

(73) Assignee: Sturm Maschinen- & Anlagenbau GmbH, Salching (DE)

( * ) Notice: Subject to any disclaimer, the term of this patent is extended or adjusted under 35 U.S.C. 154(b) by 74 days.

(21) Appl. No.: 15/766,564

(22) PCT Filed: Oct. 6, 2016

(86) PCT No.: PCT/EP2016/073844
§ 371 (c)(1),
(2) Date: Apr. 6, 2018

(87) PCT Pub. No.: WO2017/063935
PCT Pub. Date: Apr. 20, 2017

(65) Prior Publication Data
US 2018/0299261 A1    Oct. 18, 2018

(30) Foreign Application Priority Data

Oct. 14, 2015  (EP) ..................... 15189812

(51) Int. Cl.
*G01B 11/245* (2006.01)
*G01N 21/95* (2006.01)
(Continued)

(52) U.S. Cl.
CPC .......... *G01B 11/245* (2013.01); *G01B 11/007* (2013.01); *G01B 11/026* (2013.01);
(Continued)

(58) Field of Classification Search
CPC ... G01B 11/245; G01B 11/007; G01B 11/026; G01B 11/12; G01B 11/24; G01B 11/30;
(Continued)

(56) References Cited

U.S. PATENT DOCUMENTS 6,462,815 B1    10/2002  Drabarek et al.
2007/0153296 A1  7/2007  Schick
(Continued)

FOREIGN PATENT DOCUMENTS

DE    102008050259 A1    4/2010
DE    102012204498 A1    9/2013
(Continued)

OTHER PUBLICATIONS

English Translation of the International Preliminary Report on Patentability dated Sep. 13, 2017 for PCT/EP2016/073844 filed Oct. 6, 2016. pp. 1-9.
(Continued)

*Primary Examiner* — Rebecca C Bryant
(74) *Attorney, Agent, or Firm* — Dinsmore & Shohl LLP

(57) ABSTRACT

A sensor device for the inspection of the surface of a cylindrical hollow enclosure having at least one sensor unit set up for an optical confocal distance measurement. The at least one sensor unit has an elongated shape and exhibits an external optical system, through which a measurement device in which light can be emitted and received, is disposed transversely to a longitudinal axis of this sensor unit. The sensor device additionally comprises a movement mechanism, which is adapted to move the at least one sensor unit in one direction of motion into and out of a cylindrical hollow enclosure to be inspected. Control means are provided for measuring raisings of a surface of the cylindrical hollow enclosure and are adapted to control the at least one
(Continued)

sensor unit for carrying out a first distance measurement, during which the measuring direction relative to the direction of motion is at an angle from 20° to 85°, and to control the at least one sensor unit for carrying out a second distance measurement, during which the measuring direction relative to the direction of motion is at an angle from 95° to 160°. To this end, the measuring direction of the at least one sensor unit can be at an angle between 95° and 175° relative to the longitudinal axis of said sensor unit, wherein this sensor unit is mounted on a rotatable bearing such that one and the same sensor unit can be moved to different positions of rotation for the first distance measurement and for the second distance measurement. Alternatively, the at least one sensor unit can comprise at least one first sensor unit and at least one second sensor unit, the first sensor unit being formed and linked with the movement device in such a manner that its measuring direction relative to the direction of motion is at an angle from 20° to 85°, and the second sensor unit being formed and linked with the movement device in such a manner that its measuring direction relative to the direction of motion is at an angle from 95° to 160°. In addition, a corresponding method is disclosed.

10 Claims, 4 Drawing Sheets

(51) Int. Cl.
*G01B 11/00* (2006.01)
*G01B 11/02* (2006.01)
*G01B 11/12* (2006.01)
*G01B 11/24* (2006.01)
*G01N 21/954* (2006.01)

(52) U.S. Cl.
CPC .............. *G01B 11/12* (2013.01); *G01B 11/24* (2013.01); *G01N 21/95* (2013.01); *G01N 21/954* (2013.01); *G01N 2021/9544* (2013.01); *G01N 2021/9548* (2013.01)

(58) Field of Classification Search
CPC ................. G01N 21/95; G01N 21/954; G01N 2021/9548; G01N 2021/9544
See application file for complete search history.

(56) References Cited

U.S. PATENT DOCUMENTS

| | | | |
|---|---|---|---|
| 2010/0220369 | A1 | 9/2010 | Knuettel |
| 2017/0236266 | A1* | 8/2017 | Rostami ............... H04N 5/2256 348/131 |

FOREIGN PATENT DOCUMENTS

| | | |
|---|---|---|
| DE | 102013003640 A1 | 9/2014 |
| DE | 102014201531 A1 | 7/2015 |
| EP | 15151723 A1 | 7/2016 |

OTHER PUBLICATIONS

International Search Report and Written Opinion dated Feb. 1, 2017 for PCT/EP2016/073844 filed Oct. 6, 2016.

\* cited by examiner

ID AND METHOD OF
INSPECTING THE SURFACE OF A
CYLINDRICAL HOLLOW ENCLOSURE

The present disclosure relates in a first aspect to a sensor device for the inspection of the surface of a cylindrical hollow enclosure according to the generic clause of claim 1. In a further aspect, the disclosure relates to a method of inspecting the surface of a cylindrical hollow enclosure according to the generic clause of claim 10.

Said cylindrical hollow enclosure may theoretically be an arbitrary hollow enclosure having a round cross-section, which round cross-section need not necessarily be of a precise circularity. It need not have precisely the same cross-section at one height of the cylindrical hollow enclosure. In particular, the cylindrical hollow enclosure can have a tapered shape and/or an uneven surface.

The cylindrical hollow enclosures to be inspected may in particular be work cylinders, for example cylindrical bores in an engine block of an internal combustion engine or work cylinders of a servomotor.

In particular, in the case of such cylindrical hollow enclosures, the geometrical properties should agree very exactly with specifications. In order to check this, surface inspections can be carried out on a cylindrical hollow enclosure, in particular for determining a diameter of the cylindrical hollow enclosure and for determining unevenness of the surface of the cylindrical hollow enclosure.

A generic sensor device for the inspection of the surface of such a cylindrical hollow enclosure comprises at least one sensor unit which is designed for an optical confocal distance measurement. The at least one sensor unit has an elongated shape and has an external optical system, through which a measuring direction, in which light can be transmitted and received, is disposed transversely to a longitudinal axis of said sensor unit. In addition, the sensor device comprises a movement mechanism, adapted to move the at least one sensor unit in a direction of motion into and out of a cylindrical hollow enclosure to be inspected.

Correspondingly, a generic method for inspecting the surface of a cylindrical hollow enclosure comprises at least the following steps: Moving at least one sensor unit along a direction of motion into a cylindrical hollow enclosure to be inspected; carrying out optical confocal distance measurements by means of said at least one sensor unit, which for said optical confocal distance measurement emits light in a measuring direction via an external optical system and receives light from the measuring direction; wherein the at least one sensor unit has an elongated shape and the measuring direction is located transversely to a longitudinal axis of said sensor unit; and moving-out the at least one sensor unit along said direction of motion out of the cylindrical hollow enclosure to be inspected.

A sensor device of the above type is described for example by the applicant in the European Patent Application bearing the registration number 15151723. In addition, such a sensor device is also explained below with reference to FIGS. 1A and 1B. Known sensor devices can indeed precisely determine certain geometrical properties, such as for example the diameter of a cylindrical hollow enclosure. But the possibility of determining properties of a non-smooth surface is only in a restricted scope possible.

US 2007/153296 A1 describes an optical distance-measuring means having two confocal measuring distance sensors. The measuring directions of the two distance sensors are at right angles to a longitudinal axis of the distance-measuring means and thus also at right angles to a direction of motion of the distance-measuring means in order to moving the distance-measuring means into a hollow enclosure to be inspected. US 2010/0220369 discloses a sensor device having various superstructures by which different measuring directions can be adjusted. U.S. Pat. No. 6,462,815 B1 describes an optical sensor having a single measuring direction; this is disposed transversely to a longitudinal axis and to a direction of motion of the sensor. DE 10 2008 050 259 A1 discloses a distance sensor with which two measuring directions are produced. One measuring direction is at right angles to the longitudinal axis of the sensor, the other measuring direction is disposed transversely thereto. DE 10 2013 003 640 A1 describes an optical distance-measuring sensor with which two measuring directions are produced that are disposed transversely to a longitudinal axis of the distance sensor.

As one object of the invention may be considered to indicate a method and a sensor device for inspecting the surface of a cylindrical hollow enclosure, with which it is possible to measure uneven surfaces of said hollow enclosure as precisely as possible.

This object is achieved by the sensor device having the features of claim 1 and also by the method having the features of claim 10.

According to the invention, on the aforementioned generic sensor device provision is made for measuring projections or raisings of a surface of the cylindrical hollow enclosure in that control means are provided and adapted so as to control the at least one sensor unit such to carry out a first distance measurement, in which case the measuring direction relative to the direction of motion is at an angle from 20° to 85°, more particularly from 30° to 60°, and to control the at least one sensor unit such to carry out a second distance measurement, in which the measuring direction relative to the direction of motion is at an angle from 95° to 160°, more particularly from 120° to 150°. For this can be provided, on the one hand, that the measuring direction of the at least one sensor unit is at an angle between 95° and 175°, more particularly between 105° and 150°, in relation to the longitudinal axis of this sensor unit (the external optical system of the at least one sensor unit is thus designed in such a manner that the measuring direction of this sensor unit forms the aforementioned angle), and this sensor unit is mounted on a rotatable bearing such that it is possible for one and the same sensor unit to be moved in different positions of rotation for the first and the second distance measurement. For example, the sensor unit can be designed such that its measuring direction is at an angle of 130° to the longitudinal axis. If the longitudinal axis is directed parallel to the aforementioned direction of motion, the measuring direction relative to the direction of motion is also at an angle of 130°. When the sensor unit is now tilted away by, say, 80° from the adjacent surface of the hollow enclosure to be inspected (that is to say, when an end of the sensor unit remote from the external optical system is tilted away from the adjacent surface), so results an angle of 130°−80°=50° between the measuring direction and the direction of motion.

Alternatively or additionally, the at least one sensor unit can, according to the invention, comprise at least one first and one second sensor unit, wherein the first sensor unit (for carrying out the first distance measurement) is thus designed and linked with the movement mechanism that its measuring direction relative to the direction of motion is at an angle from 20° to 85°, more particularly from 30° to 60°. At the same time, the second sensor unit (for carrying out the second distance measurement) is thus designed and linked with the movement mechanism that its measuring direction relative to the direction of motion is at an angle of from 95° to 170°, more particularly between 105° and 150°.

In the case of the method of said above type, provision is made, according to the invention, for the optical confocal distance measurement to be carried out comprises at least:

carrying out a first distance measurement by way of the at least one sensor unit for measuring protrusions on a surface of the cylindrical hollow enclosure, wherein the measuring direction for said first distance measurement relative to the direction of motion is at an angle of from 20° to 85°, more particularly from 30° to 60°, carrying out a second distance measurement by way of said at least one sensor unit for the measurement of protrusions on a surface of the cylindrical hollow enclosure, wherein the measuring direction for said second distance measurement relative to the direction of motion is at an angle of from 95° to 160°, more particularly from 120° to 150°, wherein the referred angle made available for said first and said second distance measurements is provided in that:
either
the measuring direction of the at least one sensor unit is at an angle of from 95° to 175°, more particularly from 105° to 150°, relative to the longitudinal axis of this sensor unit and this sensor unit is mounted on a rotatable bearing by means of which the same sensor unit is moved to different positions of rotation for the first distance measurement and for the second distance measurement respectively,
and/or
the at least one sensor unit comprises at least one first sensor unit and one second sensor unit,
wherein the first sensor unit is such designed and linked with the movement mechanism that its measuring direction relative to the direction of motion is at an angle from 20° to 85°, more particularly from 30° to 60°, and
wherein the second sensor unit is such designed and linked with the movement mechanism that its measuring direction relative to the direction of motion is at an angle from 95° to 170°, more particularly from 105° to 150°.

Due to the invention, non-smooth surfaces, i.e. protrusions or elevations/depressions on a surface of a cylindrical hollow enclosure, can be effectively measured. In particular, the protrusions can not only project into the cylindrical hollow enclosure in the radial direction, but can be additionally inclined in the longitudinal direction of the cylindrical hollow enclosure and more particularly have a hook-shaped or dovetailed shape. Such a surface shape is produced, for example, in the case of cylindrical hollow enclosures in an engine block. An advantage of such a shape rests in the fact that a coating to be applied obtains a higher adhesive pull strength. The creation of this non-smooth surface is in this context also referred to as "activation". Within the scope of the present description it is of no significance whether a non-smooth surface is described by raised areas on a surface, or instead by depressions in a surface. Both wordings may relate to the same surface shape.

An essential concept of the invention may be regarded in that it is possible to examine protrusions or raised areas more efficiently when the measuring direction of an employed sensor unit is not positioned perpendicularly to the surface of the cylindrical hollow enclosure to be inspected. Slanted protrusions that form an angle of, for example, 15° to a perpendicular to the surface can be particularly well measured when the measuring direction of the sensor unit is also oriented at an angle between 10° and 20° to a perpendicular to said surface. In particular in the case of work cylinders to be coated, a surface shape is formed, wherein protrusions projecting inwardly into the hollow enclosure also extend in the axial direction of the hollow enclosure and form at its ends an overhang in the axial direction. It has been found that for a precise measurement of such geometry, a single measuring direction relative to the surface is not sufficient. But rather at least two measuring directions are expedient, which for example are at an angle of +15° and −15° to a perpendicular of the surface to be inspected.

This set of problems is described in more detail with reference to FIGS. 1A and 1B. FIG. 1A illustrates diagrammatically a non-inventive investigation of a cylindrical hollow enclosure 90. This comprises a surface 91 that has been mechanically processed (activated) for the purpose of improving the grip of a coating to be applied. In this way, the surface 91 comprises raised areas or protrusions 92 having a dovetailed cross-section. These raised areas 92 project not at approximately right angles to an undersurface of the surface 91, but at an angle, as illustrated. It is desirable to measure the dimensions of these projecting raised areas 92 as precisely as possible. FIG. 1A illustrates a sensor device 1 of the prior art comprising a sensor unit 10. This operates according to the confocal principle and thus can precisely measure a distance in a measuring direction 11. The measuring direction 11 is fixed by an external optical system 13 of the sensor unit 10, in that light is emitted by this optical system 13 in the measuring direction 11 and light coming from the measuring direction 11 is guided further toward a light detector of the sensor device 1. To this end light is guided through an optical fiber 19 toward the sensor unit 10 and/or away from this. In the case of the prior sensor device 1 shown, the measuring direction 11 is at right angles to a longitudinal axis 15 of the sensor unit 10. In addition, the measuring direction 11 is at right angles to a direction of motion 31, along which the sensor unit 10 is moved into the hollow enclosure 90. As may be seen from FIG. 1A, it is hardly possible, when using a single measuring direction 11 that is at right angles to the surface 91 to be inspected, to obtain information concerning the inclination and shape of the projecting region of a protrusion 92.

It is conceivable to tilt the sensor unit 10 such that the measuring direction 11 is no longer be at right angles to the surface 91 and thus also is capable of looking behind raised protrusions 91. Such a situation is diagrammatically illustrated in FIG. 1B. When the sensor unit 10 is tilted in such a way, however, the distance of the external optical system 13 from the surface 91 to be inspected, is increased, because otherwise one end of the elongated sensor unit 10 forming the opposite end of the external optical system 13 (the upper end of the sensor unit 10 in FIG. 1B) would butt against the surface 91. Confocal distance sensors have indeed a very high measuring resolution, but also instead only a relatively small measurement range. On account of the tilting shown in FIG. 1B, the distance of the external optical system 13 from the surface 91 is beyond the measuring range of the sensor unit 10. For this reason, it is not possible for the sensor unit 10 to execute a meaningful measurement in the position shown.

This problem is overcome by the sensor device of the invention. According to the invention, already a single sensor unit can suffice. At this, the measuring direction may not, however, be at right angles to the longitudinal axis of the sensor unit. In fact, the measuring direction forms an angle between 100° and 250° to the longitudinal axis of the sensor unit. In this case, this angle is measured relatively to the longitudinal axis at the external optical system, which runs from the external optical system toward a central region of the sensor unit. An angle of 180° accordingly means that the measuring direction runs from the external optical system directly away from the center of the sensor. An angle of 0° would indicate, on the other hand, that the measuring direction would run from the external optical system into the sensor unit to the central region thereof. On account of the aforementioned inclination between the measuring direction and the longitudinal axis of the sensor unit is achieved that this can investigate protrusions in two different positions of rotation on a surface of a cylindrical hollow enclosure, without that collisions will take place with the surface or a measuring range of the confocal sensor unit will leave.

According to the present invention, provision may also be made for at least two sensor units to be present, which differ in their measuring direction. It is possible to select the two measuring directions, in particular, such that no tilting or rotation of the sensor unit is necessary in order to effectively measure projecting raised areas of the surface of a cylindrical hollow enclosure. An angle default for the measuring direction relative to the direction of motion may in this case be defined in which the two sensor units are capable of entering and leaving the hollow enclosure to be inspected. The direction of motion is a significant reference value, since in operation a cylindrical hollow enclosure to be inspected is advantageously disposed such that its longitudinal axis just agrees with the direction of motion. This ensures that the sensor unit or the sensor units can provide comparable results at all heights of the cylindrical hollow enclosure and also that the restricted measuring range of confocal distance measurement is always met.

A confocal distance measurement may be generally defined in that the sensor unit has an optical system, for example a convex lens, a lens group having an overall positive refractive power or reflecting agents such as a mirror having a light-converging effect, by means of which both the light to be emitted toward the surface to be inspected is radiated, and light returning from the surface to be inspected is passed on toward the light detector. Advantageously, this causes an illumination focus to just agree with a detection focus. Between the aforementioned optical system, which may also be referred to as a confocal optical system, and the light detector there may be also disposed a pinhole in an intermediate plane. This pinhole blocks out-of-focus light, so that the light detector can only receive light coming substantially from the area of the illuminating focus. Instead of a pinhole, it is also possible to dispose an optical fiber in the intermediate plane, which has a similar effect as a pinhole in regard to the transmission of light. Between the light source and the confocal optical system it is also possible to dispose a pinhole in an intermediate plane. Instead of or additionally to the pinhole, it is possible to use an optical waveguide, which transmits the light of the light source. In this case that end of this optical waveguide that faces the external optical system is disposed in an intermediate plane. On account of this confocal mode of operation there is achieved a particularly high measuring resolution. This is better than a resolution with other optical distance measuring devices operating, for example, according to the triangulation measurement method.

In order that the light to be verified will not pass from the confocal optical system toward the light source but in the direction of the light detector, it is advantageous that a beam splitter is available. This passes the light to be verified at least partially from the confocal optical system to the light detector and the illumination light at least partially from the light source to the confocal optical system. As beam splitter it is possible to use, for example, a partial translucent mirror, a polarization beam splitter or a color splitter that transmits or reflects light according to wavelength.

The confocal optical system may be basically identical with the external optical system but is preferably different therefrom. In this way it is possible for the external optical system to be adapted to a desired task in a simpler manner or to be replaced for this. In this way, the external optical system determines the measuring direction, in which light is emitted and also received. The external optical system may theoretically be any optical element, for example a refractive, a light-diffracting or a light-reflecting element, or it may comprise one or more of the aforementioned elements.

The measuring direction may designate an axis of a beam path, along which light is emitted from the external optical system. Usually, light is emitted in the shape of a cone in which the cone shape forms an aperture angle towards the measuring direction and the measuring direction passes in center through the cone. An emission of light in the measuring direction may thus be understood so to mean that light is emitted in the form of a cone surrounding the measuring direction. Along the measuring direction there is produced, at a certain distance from the external optical system, a focal point of minimum cross-section of the light beam, which may, in particular, be determined by the focal optical system.

Each sensor unit may be provided in each case with a light source and in each case with at least one light detector. The light source and the light detector may be accommodated within the elongated body of the sensor unit. Alternatively, the light source and the light detector are located outside said elongated body of the sensor unit. By way of the optical waveguide it is then possible to conduct light from the light source to the elongated body and thence via the confocal optical system to the external optical system. In the reverse direction, it is possible for the light to be verified to conduct via the external optical system to the confocal optical system and further via the optical waveguide or waveguides to the light detector.

In the case of a confocal measurement, emitted light illuminates a region of a surface of the cylindrical hollow enclosure. Light back-scattered from the illuminated region, more particularly diffused and/or reflected light, is measured by the light detector. This requires no spatial resolution. Thus the light detector need not be a camera, but it can consist, in particular, of a single photosensitive element. Thus there is produced exactly one measured value for the illuminated region, unlike a widefield illumination having a spatially resolving light detector, which for one illuminated region produces innumerable measurement values according to the number of its receiving elements. Compared with such a widefield illumination, the confocal measurement used by the invention offers distinctly higher measuring accuracy, more particularly in regard of distance information.

The elongated shape of a sensor unit may thus be understood to mean that a housing or external dimensions of said sensor unit are at least twice or three times as large as a dimension in a direction at right angles thereto. The longitudinal axis is defined as an axis which extends along the elongated shape, that is to say, in particular, in the direction in which the sensor unit has its largest dimension. End faces of the elongated shape may in particular be definite at one side by the external optical system and at the opposite side by connecting means for one or more optical fibers.

In order to move the at least one sensor unit to a measuring position, use is made of a movement mechanism. This may be designed in any desired manner in case the at least one sensor unit is capable of moving in a certain, more particularly a linear, direction of motion. This direction of motion can agree with a longitudinal axis of a cylindrical hollow enclosure to be inspected. The movement mechanism may also be accordingly designed to move the at least one sensor unit additionally in directions transverse or at right angles to the said direction of motion. This may be desirable in order to, first of all, position the at least one sensor unit over a cylindrical hollow enclosure to be inspected and then to move in the at least one sensor unit in the direction of motion into said cylindrical hollow enclosure. Expediently, the movement mechanism comprises for this purpose at least one drive, for example a motor, a magnetic linear drive or another setting element.

In the case of a preferred embodiment of the sensor device according to the invention, the first sensor unit, more particularly its external optical system, is designed such that its measuring direction relative to its longitudinal axis is at an angle between 20° and 85°, more particularly between 30° and 80°. Furthermore, the second sensor unit, more particularly its external optical system, can be designed such that its measuring direction relative to its longitudinal axis is at an angle between 95° and 160°, more particularly between 100° and 150°.

The external optical system of a sensor unit can be advantageously disposed in the longitudinal direction in an end region of the appertaining sensor unit. The angle specifications throughout the present text may thus be understood so as to mean that at an angle of 0° relative to the longitudinal direction, the measuring direction will point straight into the sensor unit, and at an angle of 180° it will point straight out of the sensor unit in the longitudinal direction. Due to the two sensor units, whose measuring directions relative to their longitudinal axes are designed differently, it is possible to examine raised areas particularly well on surface walls of the cylinders, particularly those which are produced for internal combustion engines. Besides, by the aforementioned angle ranges is achieved that a longitudinal dimension of a sensor unit is not or is only scarcely cumbersome during insertion of the sensor unit into a hollow enclosure to be inspected.

In addition, it is possible to make provision for the longitudinal axes of the first and second sensor units to be disposed substantially parallel to each other and for their longitudinal axes to be oriented substantially parallel to the direction of motion. The expression "substantially parallel" may be angles of up to 15° or preferably of up to 5°. When the sensor units are oriented parallel to each other and parallel to the direction of motion, the space required with regard to a cross-section of the hollow enclosure to be inspected is especially small. This is advantageous when the sensor device is to have further sensors available that are likewise to be moved into the cylindrical hollow enclosure.

In the case of a preferred embodiment, the first and second sensor units are identically shaped and disposed such that one is rotated with respect to the other. In particular it is possible in this case for the two sensor units to be identical except for their direction of rotation. This simplifies the manufacture. Such rotation between the sensor units can be about an axis which is disposed transversely or at right angles to the aforementioned direction of motion (and thus transversely or at right angles to the longitudinal axis of the hollow cylinder to be inspected).

In another preferred embodiment, each sensor unit comprises a superstructure with mechanical connecting means for the attachment of the superstructure to a base frame of this sensor unit, wherein the superstructure contains the external optical system of this sensor unit. For the purpose of effectuating different measuring directions, it is thus sufficient to use different superstructures on otherwise identical sensor units. In addition, it is possible to provide the same sensor units with different superstructures, depending on their use. The superstructure can comprise, as mechanical fastening means, for example a screw thread or may be formed such that it is retained on the base frame by means of a press fit. The base frame may be regarded, in particular, as that part of a sensor unit in which the optical elements necessary for a confocal image are contained, while the external optical system in the superstructure substantially causes only a beam diversion.

Preferably, the superstructure of the first sensor unit and the superstructure of the second sensor unit differ in the measuring direction, which is specified by the respective external optical system relative to an optical path within a base frame of the respective sensor unit. For example, it is possible for the external optics of two superstructures to be formed by differently tilted mirror surfaces. Apart from their external optical systems, the different superstructures could be identical.

The measuring direction of the first sensor unit and the measuring direction of the second sensor unit preferably form relatively to each other an angle from 15° to 60°, more particularly an angle between 18° and 45°. In this case, it is possible for the angle to be defined in a plane which angle is determined by the direction of motion and by the measuring direction of the first sensor unit; if the measuring direction of the second sensor unit is not in this plane, a projection of this measuring direction onto the said plane is used for determining the angle specification. In this way, an angle of rotation between the sensor units around the measuring direction stays disregarded.

In another preferred embodiment, a motorized device is provided and adapted so as to rotate the sensor unit mounted by a pivot bearing to different rotation positions for the first and second distance measurements. Expediently, it is in this case possible to provide a holder, on which the sensor unit is rotatably mounted, can be moved in, via the movement mechanism, more particularly linearly, into a hollow cylinder to be inspected, whereupon the motorized device can rotate the sensor unit within the hollow enclosure to be inspected. Thus it is possible for a single sensor unit to suffice in a simple manner in order to precisely carry out the first and second distance measurements.

The first and second distance measurements differ from each other in the present text by the measuring directions. In order to investigate a cylindrical hollow enclosure by way of its height, it is possible to provide a motion of the sensor unit or units in motion direction, in order to carry out a plurality of first distance measurements at different heights. It is likewise possible to carry out a plurality of second distance measurements. In particular, a first and a second distance measurement may take place simultaneous, when for this purpose different sensor units are used. In this case, the height position of the first distance measurement can differ from the height position of the second distance measurement carried out simultaneously.

Thus it is possible to adapt the control means so as
to move with the movement mechanism the at least one sensor unit to different height positions in the cylindrical hollow enclosure, to carry out a plurality of first distance measurements at different height positions and to carry out a plurality of second distance measurements at different height positions (in which case it is possible for the height positions of the first distance measurements to be identical with or different from the height positions of the second distance measurements), to calculate, by way of measurement results from a plurality of first distance measurements, the geometrical dimensions of raise areas of the surface of the cylindrical hollow enclosure while taking into consideration the appertaining height positions and to calculate, by way of measurement results from a plurality of second distance measurements, the geometrical dimensions of raised areas of the surface of the cylindrical hollow enclosure while taking into consideration the appertaining height positions.

The calculated geometrical dimensions may, in particular, relate to an overhang of a raised area in the direction of motion and/or to an angle at which the raised area projects. On account of the first distance measurements, it is possible, in particular, to examine an overhang of a raised area in a direction of insertion of the sensor unit into the cylindrical hollow enclosure; on the other hand, it is possible, due to the second distance measurements, in particular, to examine an overhang of a raised area in a direction of withdrawal the sensor unit.

In general, it is possible that oscillations or vibrations of the two sensor units will occur in a direction transverse or at right angles to the movement mechanism. On account of such vibrations, the distance of the sensor units from the hollow enclosure will change. The distance measurements are therefore adversely affected by such vibrations. For this reason, such vibrations are detected by at least one third sensor unit. The distance measurement data of the first and second sensor units can then be corrected in accordance with the ascertained vibrations. The statement "at least a third sensor unit" is thus to be understood as to mean that in addition to the first sensor unit and the second sensor unit there are provided one or more further sensor units. This one is or these more further are set for an optical confocal distance measurement. A measuring direction of the at least one third sensor unit can be disposed at an angle relative to the measuring directions of the first and second distance measurements within a plane at right angles to the direction of motion which angel is between 45° and 315°. The control means are now adapted so as to categorize variations in position of the first sensor unit and optionally of the second sensor unit with the aid of distance measurement data of the at least one third sensor unit operating in the plane at right angles to the direction of motion. Preferably, the optionally further third sensor units are at angles between 90° and 270° relative to the measuring directions, which are used for the first and second distance measurements, these angles being defined in the plane at right angles to the direction of motion. In addition, it is also possible for an angle of inclination from this plane outwards to be present. It is especially preferred to use a third and a fourth sensor unit. In this case, the measuring directions of these two sensor units in said plane are preferably likewise at an angle from 90° to 180° to each other. More preferably, this angle is 120° and in addition, the two measuring directions of these two sensor units form in each case an angle of 120° to the measuring directions of the first and second distance measurements. The measuring directions of the first and second distance measurements may be aligned to each other in the plane at right angles to the direction of motion, that is to say, they form an angle of 0°. This alignment may also be provided in the case of all remaining embodiments described herein.

The third sensor unit and possibly other available sensor units are mechanical linked with the first and second sensor units and are moved by the movement mechanism together with said sensor units. Thus, a distance between said sensor units is known and can, in particular, be fixed, i.e. non-changeable. This is important for being able to suggest from distance measurement data of the at least one third sensor unit to one position of all sensor units. Thus the at least one third sensor unit successively carries out distance measurements to the cylindrical hollow enclosure, wherein at vibrations between the sensor units and the cylindrical hollow enclosure can be suggested from variations in the thus obtained distance measurement data. With the aid of these position data it is possible to correct geometrical information which is gained through the first and/or second sensor units. The measuring direction of the at least one third sensor unit can lie precisely in the plane at right angles to the direction of motion. Alternatively however, it is possible for the measuring direction or measuring directions of the at least one third sensor unit to project also from the plane perpendicularly to the direction of motion, thus as described for the first and/or second sensor units. In other respects the at least one third sensor unit may, in particular, be designed identically with the first and/or second sensor unit.

The different embodiments of the sensor device of the invention are also to be regarded as advantageous variants of the method according to the invention.

In particular, method variants arise from the intended use of the sensor device.

Further advantages and features of the invention are described below with reference to the accompanying diagrammatic figures, in which FIG. 1A illustrates an example of a sensor device of the prior art.

Equal and equal acting components are usually indicated in the Figures by the same reference numerals.

Figure 1A:
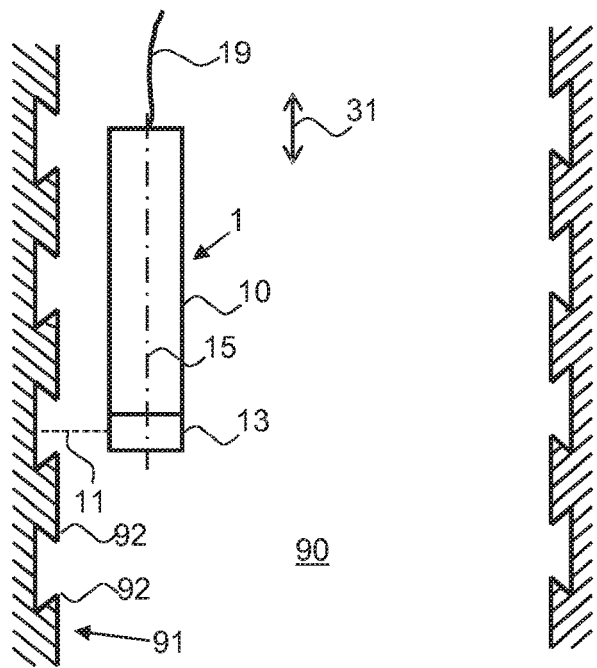
FIG. 1B illustrates the sensor device from FIG. 1A in a different alignment.
Figure 1B:
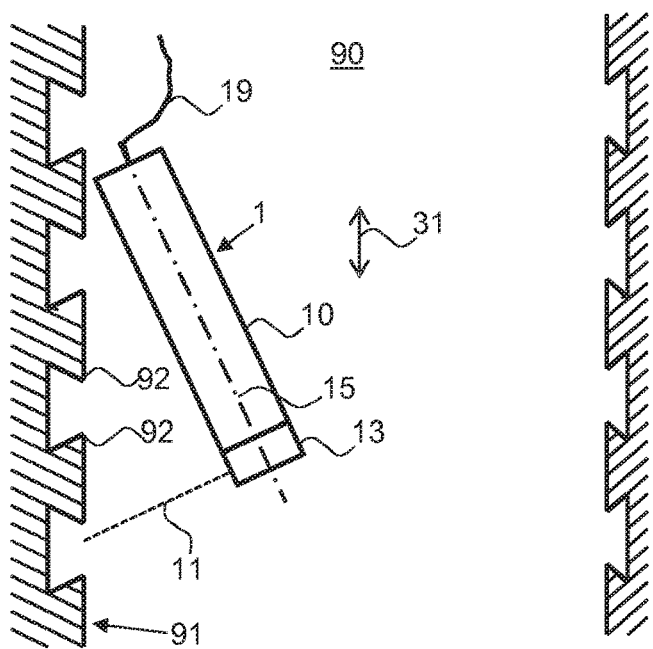

The prior sensor device 1 from the FIGS. 1A and 1B has been described above. Statements made therein concerning components of the sensor device 1 can also apply to components with the same reference numerals of embodiments of the sensor device according to the invention.

Figure 2A:
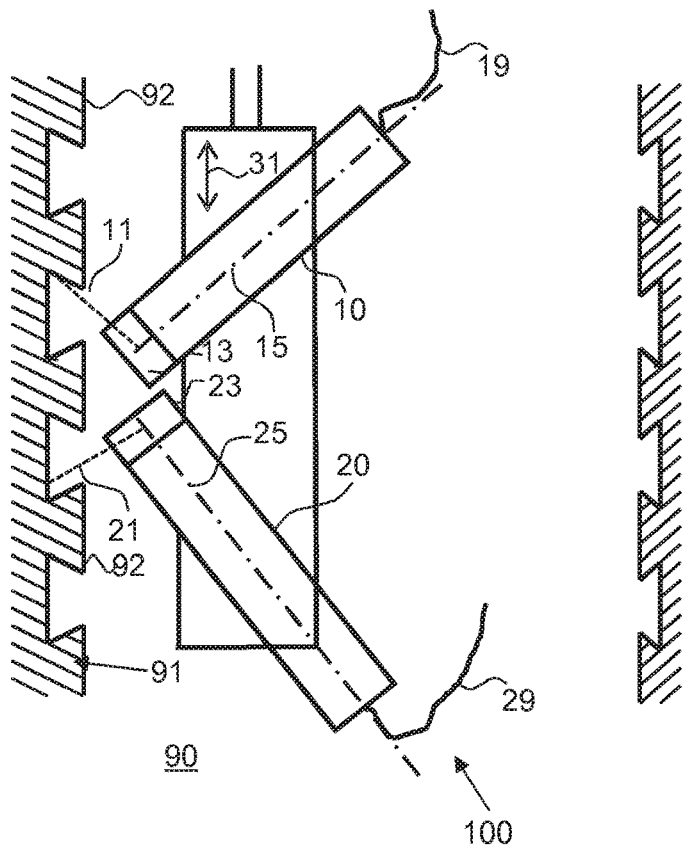
FIG. 2A illustrates an exemplary embodiment of a sensor device according to the invention.
Figure 2B:
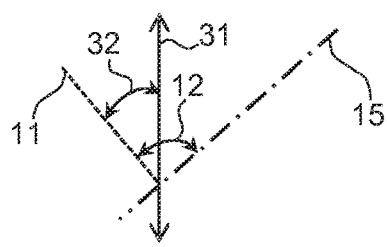
FIG. 2B shows geometrical information to FIG. 2A.
Figure 2B:
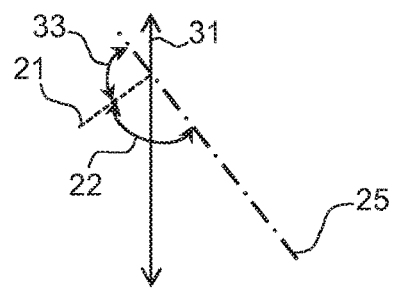

A first exemplary embodiment of a sensor device 100 of the invention is described below with reference to FIGS. 2A and 2B. FIG. 2A illustrates diagrammatic components of the sensor device 100 which are moved into a hollow enclosure 90 to be inspected. FIG. 2B serves to demonstrate certain angles to the sensor device 100 from FIG. 2A.

The sensor device 100 comprises two sensor units 10 and 20 which are in each case set for carrying out a confocal distance measurement.

To this end, the sensor device 100 has one or more light sources (not shown) available, the light of which is conducted via optical waveguides or optical fibers 19 and 29 to the two sensor units 10 and 20. Each of the sensor units 10 and 20 comprises a confocal optical system (for example a lens or lens group), which produces a focal point of the emitted light. The sensor units 10 and 20 in each case additionally have an external optical system 13 and 23 available, which sets a measuring direction 11 and 21, that is to say, an emission direction for light coming from the confocal optical system. The emitted light illuminates a surface 91 of the hollow enclosure 90 to be inspected. In this way light is back-scattered and/or reflected. This reflected light is again conducted further via the external optical system 13 and 23 and the respective confocal optical system toward a light detector (not shown). For example, it is possible for the back-scattered light to be conducted to light detectors via the optical fibers 19 and 29, which detectors are not moved into the hollow enclosure 90 to be inspected.

It may be advantageous when each of the sensor units 10 and 20 has a light detector available, which is contained in the elongated body of the sensor unit 10 or 20, while a light source is disposed outside the sensor units 10 and 20 and is linked therewith via optical fibers 19 and 29.

Within the scope of the present description an optical fiber 19, 29 may also be understood to mean a bundle comprising a plurality of fibers, which, in particular, can independently from each other conduct illumination light from the light source and the back-scattered light to be verified.

In FIG. 2A, the two sensor units 10 and 20 are mounted on a common carrier. This can be moved in the movement direction 31. In this way, it is possible for the sensor units 10 and 20 to be moved-in along the direction of motion 31 into the hollow enclosure 90 to be inspected and to be withdrawn therefrom again following done investigation. This takes place by means of a movement mechanism (here not shown), which during the measuring operation is disposed outside the hollow enclosure 90 to be inspected. Expediently, the direction of motion 31 just corresponds to the longitudinal axis or cylinder axis of the cylindrical hollow enclosure 90.

An essential idea of the invention consists in that the measuring directions 11 and 21 of the two sensor units 10 and 20 are oriented such that in the measuring operation they are not perpendicular, but are tilted to a surface 91 of the hollow enclosure 90. A microstructure of the surface 91, that is to say depressions and/or raisings of the surface 91, are shown in the Figures on an enlarged scale for illustrative purposes. The phrase "perpendicular" should not be understood in reference to such a microstructure, but in reference to a larger area of the surface 91.

The two measuring directions 11 and 21 are at an angle to each other, which can be between 15° and 40°, preferably between 18° and 30°. In this case the angle is defined in a plane that includes the direction of motion 31 and thus the cylinder axis. Thus an angle of rotation between the measuring directions 11, 21 about the cylinder axis is irrelevant. It is basically possible for such an angle of rotation to be formed in the case of all embodiments described.

The orientation of the measuring directions 11 and 22 from FIG. 2A will be explained in greater detail with reference to FIG. 2B. The sensor unit 10 has a longitudinal axis 15, to which the measuring direction 11 is at an angle 12. The sensor unit 20 has a longitudinal axis 25, to which the measuring direction 21 is at an angle 22. In the example shown, it is possible for the two sensor units 10 and 20 to be identically designed such that the angles 12 and 22 can match. However, the two sensor units 10 and 20 are rotated relatively to each other. As a result, their longitudinal axes 15 and 25 are not parallel to each other and form different angles to the direction of motion 31. For this reason, the measuring direction 11 is at an angle 32 to the measuring direction 31, which differs from an angle 33 in which the measuring direction 21 is relative to the direction of motion 31. The angle 32 can be between 70° and 85°, while the angle 33 can be between 95° and 110°.

If a measuring direction is in the angular range as stated for angle 32, an appertaining distance measurement will also be designated as a first distance measurement. If on the other hand a measuring direction is in the angular range as stated for angle 33, an appertaining distance measurement will be designated as a second distance measurement.

As illustrated in FIG. 2A, it is possible with this alignment to emit light behind projecting protrusions 92 of the surface 91 and to receive light back-scattered from there. This is on the other hand not possible in the case of a measuring direction that is perpendicular to the surface of the hollow enclosure 90, as is the case in FIG. 1A.

Figure 3:
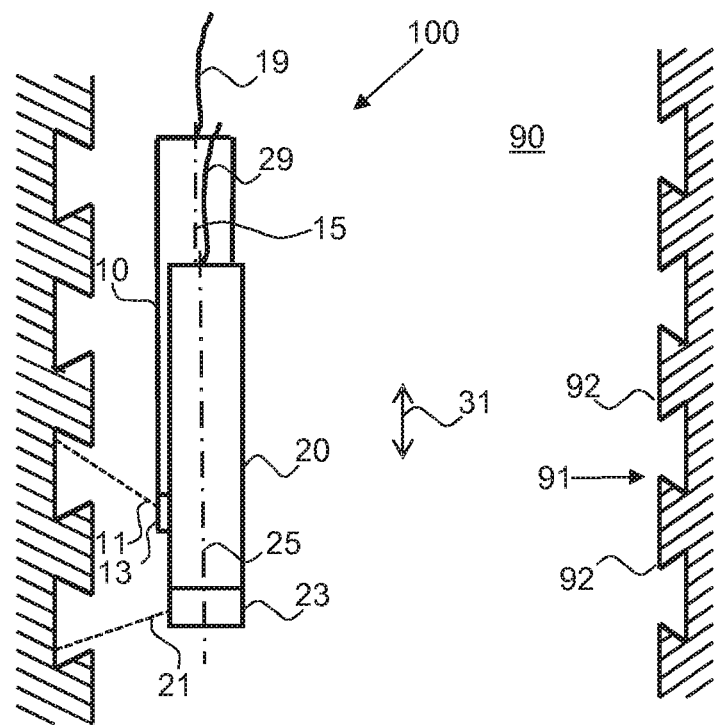
FIG. 3 illustrates another exemplary embodiment of a sensor device according to the invention.

A further exemplary embodiment of a sensor device 100 according to the invention is shown diagrammatically in FIG. 3. This sensor device largely corresponds to the sensor device shown in FIG. 2A and differs from this in the respective external optical systems 13 and 23 of the two sensor units 10 and 20. In FIG. 3 the two sensor units exhibit different external optical systems 13 and 23, which effect different light-deflection directions. In this way an angle 12 which is formed in FIG. 3 between the measuring direction 11 and the longitudinal axis 15 as explained with reference to FIG. 2B, is different from an angle 22 which is formed between the measuring direction 21 and the longitudinal axis 25. On the other hand it is possible for the angles 32 and 33 which are defined between a measuring direction 11, 21 and the direction of motion 31, to be such as described with reference to FIG. 2B. Thus in FIG. 3 the measuring directions 11, 12 are at different angles with respect to the surface 91 to be inspected and to the direction of motion 31. The two longitudinal axes 15 and 25 can on the other hand, in particular, be disposed parallel to each other and/or parallel to the direction of motion 31. As a result, the spatial requirement in a plane at right angles to the direction of motion 31 is low. Instead of a parallel arrangement, deviations are also possible of up to 20°, for example, by which exists still a relatively low spatial requirement in the said plane.

Further sensor units may be present in addition to the two shown. But, alternatively, it is also possible for the two aforementioned measuring directions 11 and 21 to be successively adjusted by means of a single sensor unit 10. This is the case in a further exemplary embodiment of the sensor device 100, which is shown in two different adjustments in FIGS. 4A and 4B.

The sensor device 100 again comprises a sensor unit 10, which external optical system 13 determines a measuring direction 11 relative to the longitudinal axis 15 of this sensor unit 10. An angle 12 between the measuring direction 11 and the longitudinal axis 15 is in this case greater than 90° and preferably is between 100° and 250°.

In this respect this sensor unit 10 differs from the known sensor unit from FIG. 1A by which the measuring direction is at right angles to the longitudinal axis. Through an angle between 98° and 110° it is possible, as illustrated in FIG. 4A, to measure behind projecting protrusions 92, without that it is necessary to incline an end of the elongated sensor unit 10 that is opposite to the external optical system 13 toward the surface 90 to be inspected, as is the case in FIG. 1B.

Figure 4A:
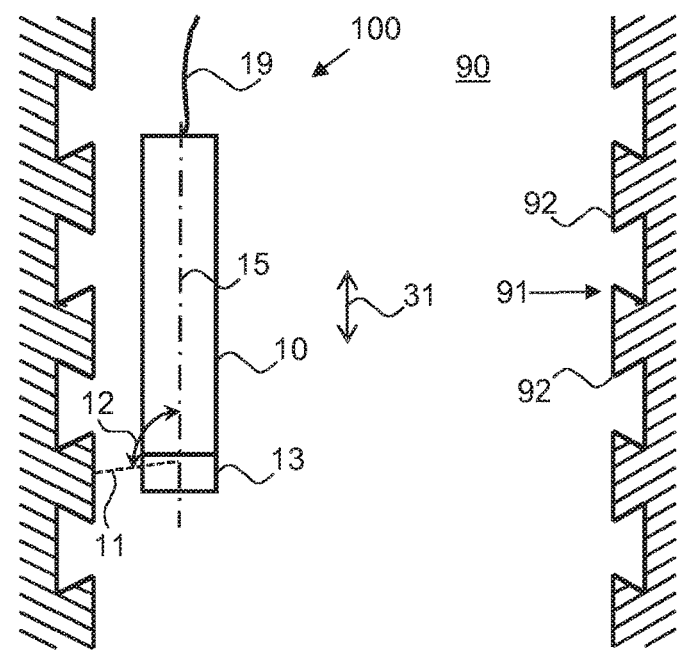
FIG. 4A illustrates again another exemplary embodiment of a sensor device according to the invention in a first measuring position.
Figure 4B:
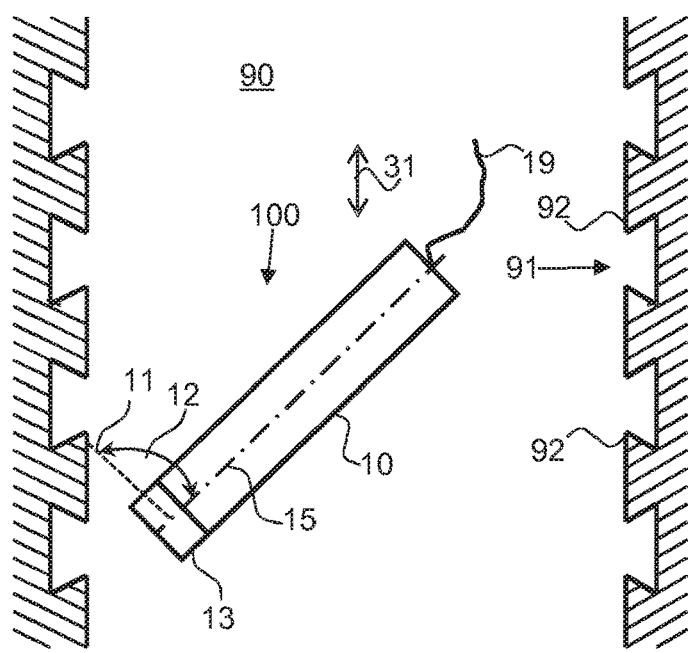
FIG. 4B illustrates the sensor device from in FIG. 4A in a second measuring position.

The sensor unit 10 from FIG. 4A is now rotatably mounted with the rotation axis being disposed transversely or at right angles to the direction of motion 31. In this way it is possible for the sensor unit to be brought into a rotational position such as is illustrated in FIG. 4B. In this rotational position a first distance measurement is possible, whereas the rotational position from FIG. 4A enables a second distance measurement. It is thus advantageously possible for the two distance measurements described above in detail to be carried out by only a single sensor unit 10.

In addition to the sensor units 10, 20 shown herein, it is possible for the sensor device 100 to comprise further sensor units whose measuring directions differ from the measuring directions 11, 21 in a plane at right angles to the direction of motion 31. These further sensor units serve to control the position of the sensor units 10 and 20. Thus the further sensor units measure in each case a distance to the cylindrical hollow enclosure, wherein from variations in these measured distances can be concluded to vibrations of all sensor units relatively to the cylindrical hollow enclosure. The knowledge of said vibrations can be used for correcting measurement data of the first and second distance measurements of the sensor units 10, 20.

With the sensor device 100 according to the invention is advantageously reached that valuable geometrical information concerning uneven surfaces of a hollow enclosure, more particularly of a cylindrical hollow enclosure, can be gathered.

The invention claimed is:

1. A sensor device for the examination of the surface of a cylindrical hollow enclosure
    having at least two sensor units, which are in each case set up for an optical confocal distance measurement,
    wherein the at least two sensor units comprise at least one first sensor unit and at least one second sensor unit,
    wherein the at least two sensor units have in each case a light source and a light detector, or an optical waveguide and
    wherein the at least two sensor units in each case have an elongated shape and contain an external optical system, through which in each case a measuring direction, in which light can be irradiated and be received, stands transverse to a longitudinal axis of the respective sensor unit,
    having a movement mechanism, which is adapted to move the at least two sensor units in one direction of motion into and out of a cylindrical hollow enclosure to be examined,
    wherein
    control means are provided for scanning protrusions on a surface of the cylindrical hollow enclosure and are adapted to control the first sensor unit for carrying out a first distance measurement, during which the measuring direction relative to the direction of motion is at an angle from 20° to 85°, and are adapted to control the second sensor unit for carrying out a second distance measurement, during which the measuring direction relative to the direction of motion is at an angle from 95° to 160°,
    that the first sensor unit is formed in such a manner and linked with the movement mechanism that its measuring direction relative to the direction of motion is at an angle from 20° to 85°,
    that the second sensor unit is formed and linked with the movement mechanism in such a manner that its measuring direction relative to the direction of motion is at an angle from 95° to 160°,
    that at least one third sensor unit is provided, which is set for an optical confocal distance measurement,
    that a measuring direction of said at least third sensor unit forms, relatively to the measuring directions of the first and second distance measurements, an angle within a plane at right angles to the direction of motion, which measures between 45° and 315°,
    that the control means are adapted such that with the aid of distance measurement data of the at least third sensor unit variations in position of the first and, second sensor unit are determined in a plane at right angles to the direction of motion.

2. A sensor device according to claim 1,
wherein
the first sensor unit is formed in such a manner that its measuring direction relative to its longitudinal axis is at an angle from 20° to 85°,
that the second sensor unit is formed in such a manner that its measuring direction relative to its longitudinal axis is at an angle from 95° to 160°.

3. A sensor device according to claim 1,
wherein
the first and second sensor units with their longitudinal axes are disposed substantially parallel to each other and their longitudinal axes are oriented substantially parallel to the direction of motion.

4. A sensor device according to claim 1,
wherein
the first and second sensor units are identically formed and are disposed rotated to each other.

5. A sensor device according to claim 1,
wherein
each sensor unit has a superstructure with mechanical connecting means for the attachment of the superstructure to a base element of said sensor unit and
that the superstructure contains the external optical system of said sensor unit.

6. A sensor device according to claim 5,
wherein
the superstructure of the first sensor unit and the superstructure of the second sensor unit differ as to the measuring direction, which is specified by the respective external optical system.

7. A sensor device according to claim 1,
wherein
the measuring direction of the first sensor unit and the measuring direction of the second sensor unit form an angle from 15° to 40° to each other.

8. A sensor device according to claim 1,
wherein
a driving system is provided and is adapted to rotate at least one sensor unit, mounted on a rotatable bearing, in different rotary positions for the first and second distance measurement.

9. A sensor device according to claim 1,
wherein
the control means are further adapted thereto
    by means of the movement mechanism the at least two sensor units are moved to different height positions in the cylindrical hollow enclosure,
    a plurality of first distance measurements are carried out at different height positions and a plurality of second distance measurements are carried out at different height positions,
    using measurement results of a plurality of first distance measurements while taking into consideration the appertaining height positions for calculating geometrical dimensions of protrusions of the surface of the cylindrical hollow enclosure and using measurement results of a plurality of second distance measurements while taking into consideration the appertaining height positions for calculating geometrical dimensions of protrusions of the surface of the cylindrical hollow enclosure.

10. A method of examining the surface of a cylindrical hollow enclosure, in which at least the following steps are carried out:
    moving-in at least two sensor units along a direction of motion into a cylindrical hollow enclosure to be examined,
    carrying out optical confocal distance measurements by means of each of the at least two sensor units, which in each case, for the optical confocal distance measurement, emits light in a measuring direction via an external optical system and receives light from said measuring direction,
    wherein the at least two sensor units comprise at least one first sensor unit and one second sensor unit and in each case exhibit a light source and a light detector, or an optical waveguide,
    wherein the at least two sensor units have an elongated shape and the respective measuring direction is disposed transversely to a longitudinal axis of the respective sensor unit,
    moving-out the at least two sensor units along said direction of motion out of the cylindrical hollow enclosure to be examined,
    wherein
    the execution of the respective optical confocal distance measurements involves:
    carrying out a first distance measurement by means of the first sensor unit for scanning protrusions of a surface of the cylindrical hollow enclosure, wherein the measuring direction during the first distance measurement is at an angle from 20° to 85° relative to the direction of motion,
    carrying out a second distance measurement by means of the second sensor unit for scanning protrusions of a surface of the cylindrical hollow enclosure, wherein the measuring direction during the second distance measurement is at an angle from 95° to 160° relative to the direction of motion,
    wherein for providing the angle called for the first and second distance measurement:
    the first sensor unit is formed such and connected to the motion device that their measurement direction is relative to the motion direction in an angle from 20° to 85°, and
    the second sensor unit is formed such and connected to the motion device that their measurement direction is relative to the motion direction in an angle from 95° to 160°,
    carrying out an optical confocal distance measurement with at least one third sensor unit wherein a measuring direction of the at least third sensor unit forms, relatively to the measuring directions of the first and second distance measurement, an angle within a plane at right angles to the direction of motion, which angle is between 45° and 315°,
    determining position deviations of the first and second sensor units in the plane at right angles to the direction of motion with the aid of measured distance data produced by the at least third sensor unit.

* * * * *